United States Patent
Tuunanen

[11] Patent Number: 5,942,124
[45] Date of Patent: Aug. 24, 1999

[54] MAGNETIC PARTICLE TRANSFER DEVICE

[75] Inventor: Jukka Tuunanen, Helsinki, Finland

[73] Assignee: Labsystems, Oy, Helsinki, Finland

[21] Appl. No.: 08/817,531

[22] PCT Filed: Oct. 20, 1995

[86] PCT No.: PCT/FI95/00578

§ 371 Date: Jun. 6, 1997

§ 102(e) Date: Jun. 6, 1997

[87] PCT Pub. No.: WO96/12959

PCT Pub. Date: May 2, 1996

[30] Foreign Application Priority Data

Oct. 20, 1994 [FI] Finland ..................................... 944938

[51] Int. Cl.⁶ .................................................. B01D 35/06

[52] U.S. Cl. ........................... 210/695; 210/222; 436/526

[58] Field of Search .................... 210/222, 695; 436/526

[56] References Cited

U.S. PATENT DOCUMENTS

| | | | |
|---|---|---|---|
| 2,471,764 | 5/1949 | Miller et al. .............................. | 294/65.5 |
| 3,904,482 | 9/1975 | Mehl ....................................... | 195/109 |
| 3,970,518 | 7/1976 | Giaever .................................... | 195/1.5 |
| 3,985,649 | 10/1976 | Eddelman . | |
| 4,018,886 | 4/1977 | Giaever .................................... | 424/12 |
| 4,115,535 | 9/1978 | Giaever ..................................... | 424/1 |
| 4,200,613 | 4/1980 | Alfrey et al. ............................. | 422/71 |
| 4,272,510 | 6/1981 | Smith et al. . | |
| 4,438,068 | 3/1984 | Forrest ..................................... | 422/61 |
| 4,495,151 | 1/1985 | Ohyama et al. .......................... | 422/102 |
| 4,649,116 | 3/1987 | Daty et al. . | |
| 4,731,337 | 3/1988 | Luotola et al. ........................... | 436/526 |
| 4,751,053 | 6/1988 | Dodin et al. .............................. | 422/101 |
| 4,891,321 | 1/1990 | Hubscher .................................. | 435/293 |
| 4,895,650 | 1/1990 | Wang ....................................... | 210/222 |
| 5,167,926 | 12/1992 | Kimura et al. ........................... | 422/67 |
| 5,200,084 | 4/1993 | Liberti et al. ............................ | 210/695 |
| 5,206,034 | 4/1993 | Yamazaki ................................. | 425/145 |
| 5,318,914 | 6/1994 | Matte et al. .............................. | 436/526 |
| 5,466,574 | 11/1995 | Liberti et al. . | |
| 5,474,742 | 12/1995 | Tuuminen ................................. | 422/63 |
| 5,647,994 | 7/1997 | Tuunanen et al. ....................... | 210/695 |

FOREIGN PATENT DOCUMENTS

| | | |
|---|---|---|
| 0027008 A1 | 4/1981 | European Pat. Off. . |
| 0186001 | 7/1986 | European Pat. Off. . |
| 0042755 B1 | 8/1988 | European Pat. Off. . |
| 0317286 | 5/1989 | European Pat. Off. . |
| 0351857 | 1/1990 | European Pat. Off. . |
| 0358948 | 3/1990 | European Pat. Off. . |
| 0479448 | 4/1992 | European Pat. Off. . |
| 0522322 A1 | 1/1993 | European Pat. Off. . |
| 2824742 A1 | 2/1979 | Germany . |
| 58-5656 | 1/1983 | Japan . |
| 58-5657 | 1/1983 | Japan . |
| 58-5658 | 1/1983 | Japan . |
| 63-5263 | 1/1988 | Japan . |
| 63-5265 | 1/1988 | Japan . |
| 63-5266 | 1/1988 | Japan . |
| 1414479 | 11/1975 | United Kingdom . |
| 2147 698 | 5/1985 | United Kingdom . |
| 2147898 | 5/1985 | United Kingdom . |
| WO 86/06493 | 11/1986 | WIPO . |
| WO 87/05536 | 9/1987 | WIPO . |
| WO 94/18565 | 8/1994 | WIPO . |
| WO 9418564 | 8/1994 | WIPO . |
| WO 9418565 | 8/1994 | WIPO . |
| WO 95/00247 | 1/1995 | WIPO . |
| WO 9612958 | 5/1996 | WIPO . |
| WO 9612959 | 5/1996 | WIPO . |
| WO 9612960 | 5/1996 | WIPO . |
| WO 9612961 | 5/1996 | WIPO . |

*Primary Examiner*—David A. Reifsnyder
*Attorney, Agent, or Firm*—Fish & Richardson P.C.

[57] ABSTRACT

The invention relates to a means for separating magnetic particles from a composition and for transferring them into a liquid in a vessel. The means comprises an elongated body (1) that comprises a device which can be used to align the longitudinal magnetic field of a protective cover with the lower end of the cover and eliminate the effect of the field from the lower end, and a tip part (8) at the lower end of the body, which is tapered in a concave manner. The means is especially well-adapted for transferring particles to very small vessels. The invention can be used in different applications, especially in the fields of biotechnology, biochemistry, and biomedicine.

21 Claims, 2 Drawing Sheets

MAGNETIC PARTICLE TRANSFER DEVICE

TECHNICAL FIELD

The invention relates to the separation of magnetic particles from a composition containing them and the transferring of them to a liquid. The invention can be used in different applications, especially in the fields of biotechnology, biochemistry, and biomedicine.

BACKGROUND OF THE INVENTION

Magnetic microparticles are used as a solid phase in various applications to bind biomaterial. One advantage of microparticles is the large area of the solid phase and short diffusion lengths. The size of microparticles is generally 0.05–10 $\mu$m and they are available in different materials and already activated for many applications. Magnetic particles can be moved by using a magnetic field.

The separation methods of magnetic particles presently used include settling a reaction vessel in a magnetic field so that particles are accumulated into a so-called pellet at the bottom of the vessel. Thereafter, the liquid which is free from particles is decanted or removed by aspiration. However, the removal of the liquid from the vessel must be carried out very carefully so as not to remove the particles at the same time.

Publication EP-140787 (corresponding publication U.S. Pat. No. 4,649,116) proposes a method by which magnetic particles are separated from a liquid by using a magnetic rod which is pushed into the liquid. The particles are pulled off the rod by using a stronger magnet.

Publication WO-87/05536 suggests a device for separating magnetic particles which contains a rod movable in a vertical bore and provided with a magnet at the lower end thereof. The device is introduced into a liquid containing particles with the magnet in a lower position, whereby particles are collected at the end of the rod. When the magnet is allowed in an upper position, particles can be detached from the rod. In this way, particles can be collected and transferred from one liquid to another. The tip of the device is shaped like a cylinder tinner than the arm.

Publication WO-94/18565 proposes an assay method in which magnetic particles are separated from a liquid by using a rod comprising a conical tip and containing a movable magnet. In the application according to FIGS. 2, the rod comprises a concave and tapering tip part but particles are collected above this tip part, as shown in FIG. 2b.

However, the proposed separation devices and methods of magnetic particles are not very well-adapted to applications in which particles have to be transferred into very small vessels. The known devices are not very well-adapted for those applications either in which particles are collected from a large volume with respect to the means of separation.

SUMMARY OF THE INVENTION

Now, a transfer device according to claim 1 has been invented. Some preferred applications of the invention are presented in the other claims.

The device according to the invention comprises an elongated body comprising a means which can be used to align a magnetic field in the direction of the body to the tip of the body when particles are to be collected on the tip and eliminate the effect of this magnetic field when particles are to be released from the tip. Such a magnetic field is especially advantageous in such cases where particles are first collected in some other way, e.g., from a concentration of particles provided on the wall of a test tube. The tip part of the body is tapered and comprises a concave surface. The height of the tip part is slightly higher than the height of the vessel in which the particles are released. The width of the tip part at the upper part thereof is slightly smaller than the diameter of the vessel. When the tip is pushed into the vessel, the surface of the liquid in it rises along the surface of the tip under the influence of surface tension. The edge of the moving liquid surface wipes the particles off the tip and into the liquid. The detachment can be improved by moving the rod. Correspondingly, when the tip is raised from the well, the surface of the liquid moves as an integral film towards the end of the tip. In this way, the liquid and particles along with it are completely detached from the tip.

The cross-section of the tip part is preferably circular but, in principle, any other shape can be considered. A wedge-like form could be for tray-like vessels of a rectangular shape, for example.

The tip is preferably sharp. Liquid can be detached from a sharp tip in the most complete way possible. Furthermore, the sharp tip facilitates the placing of the tip into a vessel when the tip will rest at the bottom of the vessel.

The body preferably comprises an elongated protective cover which comprises a movable rod provided with one rod magnet in the longitudinal direction of the protective cover. The proportion of the length of the rod magnet to its thickness is preferably at least about 2:1, preferably about 3:1, and most preferably about 12:1. Both the strength and the gradient of the magnetic field thus provided are the strongest at the end of the rod, and when the magnet is in the lower position, particles are accumulated from the composition into the tip part of the protective cover in a concentrated manner.

The rod magnet is preferably comprised of a permanent magnet and a ferromagnetic arm which comprises its extension.

The rod magnet is preferably sufficiently long so that when collecting particles, the upper end of its dipole always remains above the surface of the composition. Should particles be collected from a column higher than the dipole, it must be seen to that particles are collected to the tip first from the upper part of the column so that the upper end of the dipole is above the particles the whole time. When collecting particles from very small volumes, the magnet is preferably completely above the surface. Only the magnetic field extends to the compound and the lower flange of the tip gets completely wet when the tip is placed against the bottom of the vessel.

When the magnet is provided with a ferromagnetic arm, the magnet and the magnetised arm together serve as a long rod magnet. The arm fades out the gradient of the upper pole of the field, whereupon the upper pole does not carry out collection of particles. In this way, the long rod magnet can be manufactured at a lower cost. However, even with the ferromagnetic arm, it is preferable to use a relatively long magnet (e.g., with a length of about 2 . . . 10 times the diameter). The length of the magnet is preferably selected so that a maximum internal and permanent field strength is provided for the magnet in question.

The cross-section of the rod magnet can be circular or rectangular, for example. With respect to both the manufacture and the use, the circular shape is preferable. For instance, in this case, the twisting of the magnet around its axis has no influence. In principle, the rod can also be provided with a curved shape to simplify the moving mechanism.

The protective cover on top of the rod can have various shapes according to the use. Normally, the circular shape is the most advantageous with respect to both the manufacture and use. To increase strength, the protective cover can be made conical, which facilitates the manufacture of the cover by injection moulding. The cover is suitably manufactured from polypropylene, for example.

The junction of the magnet and the arm is preferably made so that the arm and the magnet are within one another for a short length. In this way, the formation of strong gradients on the junction, which perhaps collect particles, is avoided.

The best way to separate the particles from the liquid is to first concentrate them at one point in the vessel from where they are then collected by using the rod. The concentration can be effected by letting the particles settle under the effect of gravitation, by using a centrifugation, or by pulling the particles onto the wall of the vessel by using a magnetic field. The use of a magnet is the best way in most cases.

The invention is best applied to particles of about 1–10 82 m.

BRIEF DESCRIPTION OF THE DRAWINGS

Some advantageous applications of the invention are described by way of example in the following. The drawings of the description comprise.

DETAILED DESCRIPTION OF THE INVENTION

Figure 1:
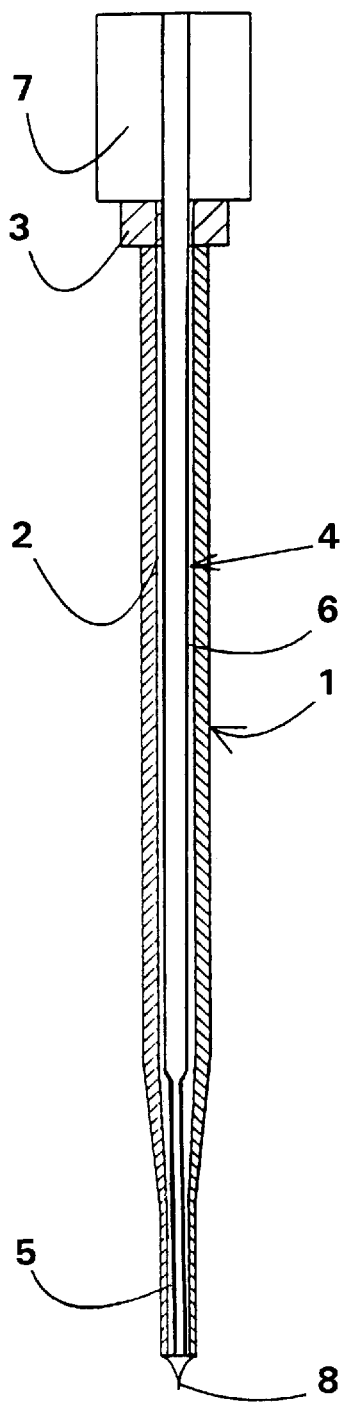
FIG. 1 which presents one separation means according to the invention.

The separating rod according to FIG. 1 comprises elongated protective cover 1 which is provided with bore 2. The lower ends of the protective cover and the bore are slightly tapered. The upper end of the body comprises gripping flange 3.

There is loose magnetic rod 4 in bore 2. The rod is provided with vertical rod magnet 5 at the lower end thereof and above that, with ferromagnetic arm 6 as an extension of the magnet. The end of the arm is provided with gripping nub 7.

The lower end of the cover is provided with tapered and sharp tip 8 with a concave surface. The length of the tip approximately corresponds to the width of the lower end of the cover.

Figure 2:
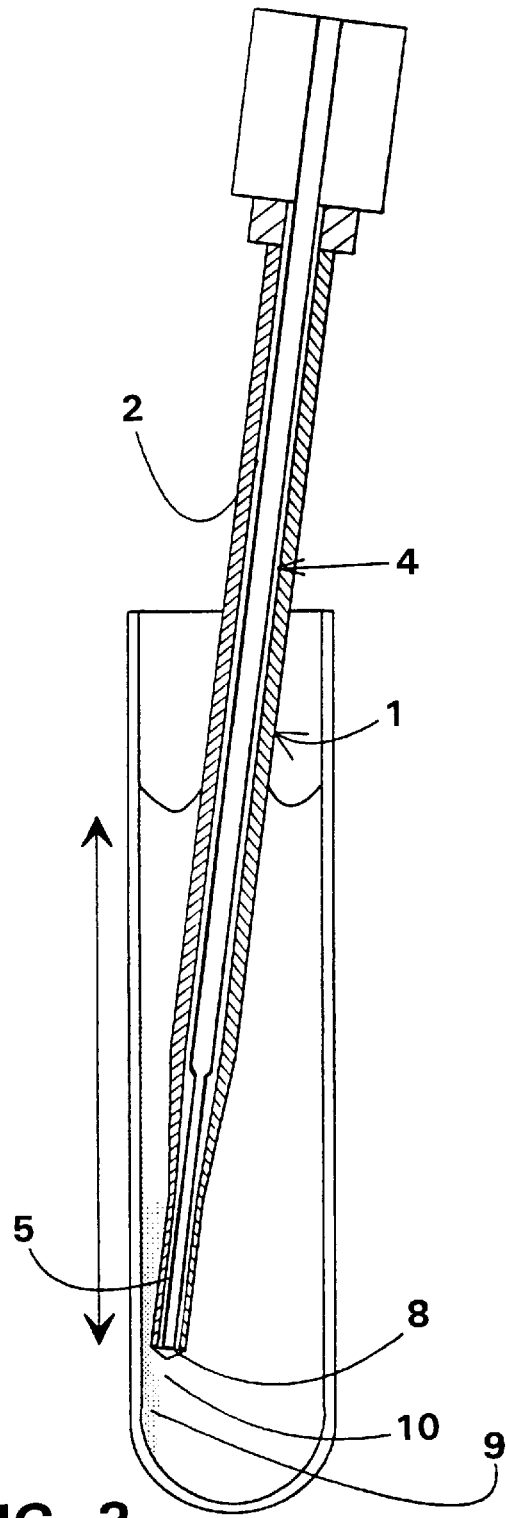
FIG. 2 which presents the use of the means of FIG. 1 for collecting particles from a suspension, FIG. 3 which presents the use of the means of FIG. 1 to release the collected particles.

FIG. 2 presents the collecting of particles from the wall of the test tube on which they were first pulled by using a magnet to form vertical strip 9. By sweeping along the strip with the tip of the rod, particles are made to adhere on the tip of protective cover 1 of the rod to form circular mass 10. When magnet 5 is kept in the lower end of bore 2, particles remain attached to the tip. When particles are to be released, the magnetic rod is lifted up.

Figures 3, 4:
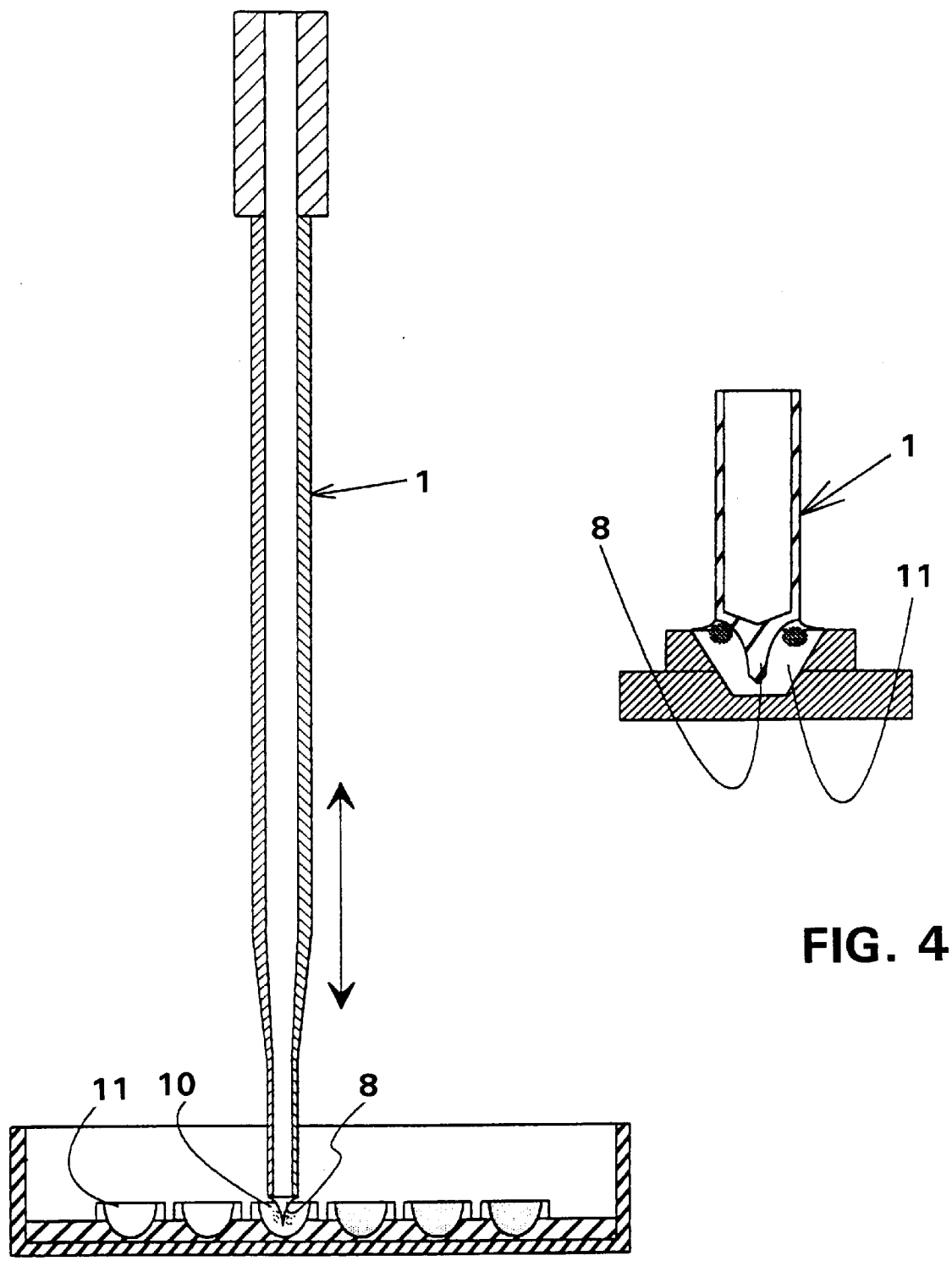
FIG. 4 which presents an enlarged detail of the tip portion of the separation part according to FIG. 1 when releasing particles into a vessel.

Tip 8 is especially well-adapted for transferring particles into a very small vessel, such as well 11 of a so-called HLA plate (FIG. 3).

FIG. 4 is an enlarged drawing of tip 8 in well 11. The tip is slightly longer than the height of the well. When the tip is pushed into the well, the surface of the liquid in it raises upwards along the surface of the tip under the effect of surface tension. The edge of the moving surface of the liquid sweeps the particles off the tip and into the liquid. The detachment can be improved by moving the rod. Correspondingly, when the tip is lifted out of the well, the surface of the liquid moves as an integral film towards the sharp end of the tip. In this way, the liquid and the particles along with it are completely detached from the tip.

When a conical well according to FIG. 4 is used, the minimum of the gap between the liquid and the tip is between the edge of the lower surface and the upper edge of the well. The liquid tries to minimise its area under the influence of surface tension, whereby the liquid settles evenly around the tip, covering the whole lower flange. The search for the minimum gap size is effected very quickly, whereby the stream of liquid sweeps the particles off the surface of the tip. When the tip is slowly detached from the liquid, the liquid seeks its minimum area every moment and the surface tends to remain integral. Finally, the end of the tip is detached from the liquid and the tip is removed from the liquid in a nearly dry state.

When releasing particles, the protective cover can be supported at its tip at the bottom of the vessel.

The proportion of the length of magnet 5 to its thickness is about 10:1 and the proportion of the length of the arm to the length of the magnet is about 5:1. The arm is slightly thicker than the magnet and the upper end of the magnet is embedded inside the lower end of the arm for a length of about twice its thickness.

I claim:

1. A device for separating magnetic particles from a composition containing them and for transferring them into a liquid in vessel, comprising:
   an elongated body adapted to receive a magnetic probe, said body including an upper end and a lower end, said lower end including
      a concave continuously tapering tip part extending to the lower end of the body, and said magnetic probe arranged to provide a magnetic field that is stronger at an end portion that is positioned proximate to said tip part.

2. A means according to claim 1, wherein said tip has a circular cross-section.

3. A means according to claim 1 wherein the elongated body has a sharp tip.

4. A means according to claim 1 wherein the lower end of the body is provided with a magnet in the longitudinal direction of the body.

5. A means according to claim 4, wherein the body comprises a magnetic rod in the longitudinal direction of the body, the proportion of the length of the rod to its thickness being at least about 2:1, preferably about 3:1.

6. A means according to claim 5, wherein the magnetic rod comprises a magnet at the lower end thereof and a ferromagnetic arm is attached to the upper end of the rod.

7. A means according to claim 6, wherein the proportion of the length of the magnetic rod to its thickness is at least about 12:1.

8. A means according to claim 6 wherein the upper end of the magnet and the lower end of the arm are inside one another.

9. A means according to any one of claims 1–8, wherein the height of the tip part is slightly higher than the height of a vessel in which the particles are released.

10. A means according to any one of claims 1–8, wherein the width of the tip part at an upper end thereof is slightly smaller than the diameter of vessel in which the particles are released.

11. A method for separating magnetic particles from a composition containing them and for transferring them into a liquid in a vessel, wherein the device used for the transfer comprises an elongated body adapted to receive a magnetic probe said body including with an upper end and a lower end, said lower end including a concave continuously tapering tip part extending to the lower end of the body, and said magnetic probe arranged to provide a magnetic field that is stronger at an end portion that is positioned proximate to said tip part comprising the steps of:

(a) collecting particles to the tip part of the body; and (b) releasing particles form said tip part by eliminating the affect of said field from said tip part.

12. A method according to claim 11, wherein the transfer means comprises a magnet including a magnet sized to be placed completely above the surface of the composition when particles are being collected.

13. An elongated magnetic probe for separating magnetic particles from a composition containing them and for transferring them into a liquid in a vessel, said probe having a concave tapering tip and providing a magnetic field that is stronger in the region of said tip than regions proximate of said tip.

14. The probe of claim 13 wherein said probe includes an elongated body having said concave tip at one end and is adapted to receive a magnet, and an elongated magnet constructed for insertion into said elongated body such that an end of said magnet is positioned proximate to said concave tip.

15. The probe of claim 14 wherein said magnet has a length to thickness ratio of about 2:1 or more.

16. The probe of claim 14 wherein said magnet has a length to thickness ratio of about 3:1 or more.

17. The probe of claim 14 wherein said magnet has a length to thickness ratio of about 12:1 or more.

18. The probe of claim 14 including a ferromagnetic arm proximate a second end of said magnet.

19. A system for manipulation of magnetic particles, comprising:

a probe as described in claim 14, and a vessel for containing magnetic particles, wherein the depth said vessel is approximately the height of said concave tip.

20. The system as described in claim 19 wherein the width of the tip is smaller than the diameter of the vessel.

21. The system of claim 19 or 20 wherein said vessel is an HLA plate.

* * * * *